United States Patent [19]

Akutagawa et al.

[11] 4,347,387
[45] Aug. 31, 1982

[54] PROCESS FOR PREPARING HYDROXYCITRONELLAL

[75] Inventors: Susumu Akutagawa, Yokohama; Takanao Taketomi, Chiba, both of Japan

[73] Assignee: Takasago Perfumery Co., Ltd., Tokyo, Japan

[21] Appl. No.: 212,964

[22] Filed: Dec. 4, 1980

[51] Int. Cl.³ .................. C07C 45/42; C07C 47/20
[52] U.S. Cl. ............................. 568/450; 568/448; 568/449; 568/485; 568/489; 252/431 P
[58] Field of Search ............ 568/450, 449, 468, 496, 568/489, 485, 448; 564/503, 509, 448; 252/431 P

[56] References Cited

U.S. PATENT DOCUMENTS

| | | | |
|---|---|---|---|
| 3,391,192 | 7/1968 | Zuech et al. | 564/509 |
| 3,437,698 | 4/1969 | O'Grady et al. | 564/509 |
| 3,465,043 | 9/1969 | Lini et al. | 568/450 |
| 3,697,580 | 10/1972 | Overwein et al. | 568/450 |
| 3,852,360 | 12/1974 | Vilkas et al. | 568/509 |
| 3,974,225 | 8/1976 | Buchi et al. | 568/450 |

FOREIGN PATENT DOCUMENTS 50-157304  7/1974  Japan ........................... 564/509

Primary Examiner—Werren B. Lone
Attorney, Agent, or Firm—Sughrue, Mion, Zinn, MacPeak & Seas

[57] ABSTRACT

A process as described for preparing hydroxycitronellal by isomerizing certain 7-hydroxygeranylamine compound or 7-hydroxynerylamine compounds using a catalyst comprising a divalent palladium compound and a phosphine compound.

11 Claims, No Drawings

PROCESS FOR PREPARING HYDROXYCITRONELLAL

This invention relates to a process for preparing hydroxycitronellal and, more particularly, to a process for preparing hydroxycitronellal by isomerizing a 7-hydroxygeranylamine compound (trans form), represented by formula (I) below, or a 7-hydroxynerylamine compound (cis form), represented by formula (II) below, to form a 7-hydroxyaldehydoenamine represented by formula (III) below, and then hydrolyzing the resulting enamine.

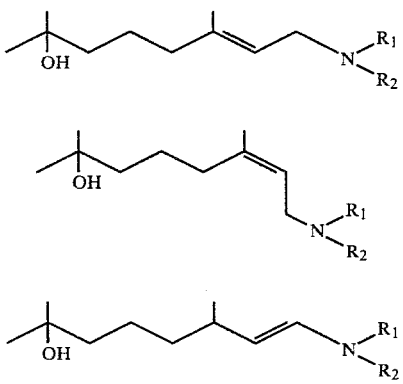

The formulae (I), (II), and (III), $R_1$ and $R_2$ each represents an alkyl group containing from 1 to 6 carbon atoms or a cycloalkyl group, or $R_1$ and $R_2$ may jointly form together with the adjacent nitrogen atom a 5- or 6-membered ring that may contain other heterocyclic atoms selected from nitrogen and oxygen.

Hydroxycitronellal is a compound useful as a perfume, and is now being produced on a large scale.

As a result of various investigations to prepare this hydroxycitronellal with industrial advantages, it has now been discovered that a 7-hydroxygeranylamine compound according to formula (I) or a 7-hydroxynerylamine compound according to formula (II) can be isomerized to form a 7-hydroxyaldehydoenamine according to formula (III) in high yield by a catalytic isomerization reaction using a catalyst composed of a divalent palladium compound and a phosphine compound.

Therefore, the present invention provides a novel process for preparing hydroxycitronellal with industrial advantages.

The 7-hydroxygeranylamine compound of formula (I) and the 7-hydroxynerylamine compound of formula (II) can be easily obtained by the conventional methods, for example, by the reaction of myrcene with dimethylamine in the presence of an alkali metal (see Japanese patent application (OPI) No. 70707/76), or the telomerization of isoprene with a secondary amine (see K. Takabe et al, *Tetrahedron Letters*, No. 39, pp 4009 (1972), or K. Takabe et al, *Bulletin of the Chemical Society of Japan*, Vol. 46, pp 218 (1973)), to form a corresponding geranylamine or nerylamine compound which is then hydrolyzed with sulfuric acid in the conventional manner.

The catalyst of the present invention is prepared from a divalent palladium compound, a trivalent organophosphorus compound, and an alkali metal phenoxide.

Examples of the divalent palladium compound include halides, nitrates, carboxylates, and chelate compounds (e.g., acetylacetonato salt) of divalent palladium.

The trivalent organophosphorous compound is a unidentate ligand represented by formula (IV)

wherein A represents an alkyl group containing from 1 to 6 carbon atoms, a cycloalkyl group, or an aryl group, and B and C each represents an alkyl group containing from 1 to 6 carbon atoms, a cycloalkyl group, or an aryl group, or B and C may jointly form together with the adjacent phosphorus atom a 5- or 6-membered ring; or the organophosphorous compound may be a bidentate ligand such as an alkylenediphosphine, wherein two phosphorus atoms are connected to each other through a carbon chain containing from 1 to 4 carbon atoms, a diphosphine wherein two phosphorus atoms form a heterocyclic ring, or a 1,1'-bisphosphinoferrocene compound wherein two phosphorus atoms are connected to each other through a ferrocenyl group. Specific examples thereof include triphenylphosphine, diphenylisopropylphosphine, 3-methyl-1-phenylphosphorene, 1,3-bis-diphenylphosphinopropane, 1,4-bis-diphenylphosphinobutane, 1,1'-bis-diphenylphosphinoferrocene and so forth.

The alkali metal phenoxide is a compound derived from unsubstituted, mono-substituted, di-substituted, or tri-substituted phenol. Examples of useful substituents include a halogen atom, a trifluoromethyl group, an alkoxy group, a cyano group, an aldehydo group, an acetyl group, a nitro group, an alkylsulfoxide group, etc. Useful substituted phenols include, for example, o-, m- or p-chlorophenol, m- or p-cyanophenol, m- or p-nitrophenol, m- or p-hydroxybenzaldehyde, o-, m- or p-bromophenol, o-, m- or p-fluorophenol, o-, m- or p-trifluoromethylphenol, 2,3-dichlorophenol, 2,4-dichlorophenol, 2,5-dichlorophenol, 3,4-dichlorophenol, 3,5-dichlorophenol, 2,4-dinitrophenol, 3,4-dinitrophenol, 3,4-dicyanophenol, 3,5-dicyanophenol, 2,3-difluorophenol, 2,4-difluorophenol, 2,5-difluorophenol, 2,3-dibromophenol, 2,4-dibromophenol, 2,5-dibromophenol, 3,4-dibromophenol, 2,3-di(trifluoromethyl)-phenol, 2,4-di(trifluoromethyl)phenol, 2,5-di(trifluoromethyl)phenol, 3,4-di(trifluoromethyl)phenol, 2-chloro-4-nitrophenol, 3-chloro-4-nitrophenol, 3-trifluoromethyl-4-nitrophenol, 3-cyano-4-chlorophenol, 3-hydroxy-4-nitrobenzaldehyde, 2-bromo-4-nitrophenol, 2,3,4-trichlorophenol, 2,3,5-trichlorophenol, 2,4,5-trichlorophenol, 3,4,5-trichlorophenol, 2,3,4-trifluorophenol, 2,3,5-tribromophenol, 3,4,5-tricyanophenol, and so forth.

In preparing the catalyst of the present invention, molar ratios of respective ingredients are important; for example, it is preferable to add from 1 to 2 mols of the trivalent organophosphorous compound per mol of divalent palladium compound, and, after dissolving in a solvent to prepare a homogeneous solution, to add thereto from 1 to 5 mols of the alkali metal phenoxide in a nigrogen stream while cooling to a temperature of from 0° C. to 10° C. As the solvent to be used, hydrocarbon series solvents or ether series solvents are preferable.

The catalyst prepared as described above has an extremely high activity. For example, the catalyst prepared from 1 mol of the palladium compound can isomerize about 5,000 mols of the 7-hydroxygeranylamine compound of formula (I) or the 7-hydroxynerlyamine compound of formula (II).

In practicing the present invention, the palladium compound is preferably used in such amount that the molar ratio of the compound of formula (I) or (II) to the palladium compound is from 1,000/1 to 5,000/1. When used in such amount, the catalyst causes the isomerization providing the 7-hydroxyaldehydoenamine (III) in a yield as high as 80 to 95%. The isomerization reaction is generally carried out at a temperature of about 140° C. to 180° C. for about 5 to 20 hours, but it is the most optimum from the economical viewpoint to carry out the reaction at 150° C. for 15 hours.

After completion of the isomerization reaction, addition of a dilute solution of a mineral acid, such as hydrochloric acid, sulfuric acid, phosphoric acid, etc., or an organic acid, such as acetic acid, etc. causes separation of hydroxycitronellal as a result of decomposition of (III). The thus formed oily layer is separated and, after extraction of the aqueous layer with an organic solvent such as benzene or the like, the oily layer and the extract are combined, followed by purification by distillation, to obtain hydroxycitronellal.

Alternatively, highly pure hydroxycitronellal can be obtained by adding, after completion of the isomerization reaction, a small amount of water or methanol to the reaction solution to deactivate the catalyst, distillating to isolate the 7-hydroxyaldehydoenamine (III), and treating the resulting enamine (III) with a dilute acid as described above.

The present invention will now be described in more detail by the following non-limiting examples.

EXAMPLE 1

100 g (441 mmols) of 7-hydroxygeranyldiethylamine was added to a catalyst prepared by treating 30 mg (0.113 mmol) of palladium nitrate, 59 mg (0.226 mmol) of triphenylphosphine and 66 mg (0.565 mmol) of sodium phenoxide in 10 ml of tetrahydrofuran, and heated to 150° C. for 15 hours to react. Then, after deactivating the catalyst by adding a small amount of water, the reaction mixture as produced was subjected to distillation under reduced pressure to obtain 91 g of 7-hydroxycitronellal diethyleneamine boiling at 95° C./1 mmHg. Addition of 2 N sulfuric acid to the resulting 7-hydroxycitronellaldiethyleneamine up to a weakly acidic level caused separation of 7-hydroxycitronellal. After distillation of the product, there was obtained 59 g (yield: 78%) of 7-hydroxycitronellal boiling at 95° C./1 mmHg.

EXAMPLES 2 TO 3

Table 1 shows results obtained in the same manner as in Example 1, except using 0.1 mmol of the palladium compounds as listed in Table 1 in place of the palladium nitrate used in Example 1, and using 12.5 g (55 mmols) of 7-hydroxygeranyldiethylamine.

TABLE 1

| Example | Palladium Compound | Yield (%) of 7-Hydroxycitronellal |
| --- | --- | --- |
| 2 | PdCl$_2$ | 70 |
| 3 | Pd(OCOCH$_3$)$_2$ | 72 |

EXAMPLES 4 TO 9

Table 2 shows results obtained in the same manner as in Example 1, except using the organophosphorous compounds listed in Table 2 in place of the triphenylphosphine used in Example 1, and using 12.5 g (55 mmols) of 7-hydroxygeranyldiethylamine.

TABLE 2

| Example | Organophosphorous Compound | (mmol) | Yield (%) of 7-Hydroxycitronellal |
| --- | --- | --- | --- |
| 4 | P(C$_6$H$_5$)(C$_2$H$_5$)$_2$ | (0.2) | 55 |
| 5 | 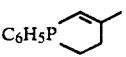 C$_6$H$_5$P | (0.2) | 40 |
| 6 | P(C$_6$H$_5$)$_2$(i-C$_3$H$_7$) | (0.2) | 48 |
| 7 | (C$_6$H$_5$)$_2$P—(CH$_2$)$_3$—P(C$_6$H$_5$)$_2$ | (0.1) | 56 |
| 8 | (C$_6$H$_5$)$_2$P—(CH$_2$)$_4$—P(C$_6$H$_5$)$_2$ | (0.1) | 50 |
| 9 | 1,1'-bis-diphenylphosphinoferrocene | (0.1) | 80 |

EXAMPLES 10 TO 13

Table 3 shows results obtained in the same manner as in Example 1, except using 0.5 mmol of the alkali metal phenoxides listed in Table 3 in place of the sodium phenoxide used in Example 1, and using 12.5 g (55 mmols) of 7-hydroxygeranyldiethylamine.

TABLE 3

| Example | Alkali metal phenoxide | Yield (%) of 7-Hydroxycitronellal |
| --- | --- | --- |
| 10 | OHC—⟨⟩—ONa | 55 |
| 11 | Cl—⟨⟩—ONa | 20 |
| 12 | O$_2$N—⟨⟩—ONa | 80 |
| 13 | O$_2$N—⟨⟩(NO$_2$)—ONa | 85 |

EXAMPLE 14

Proceeding in the same manner as in Example 1, except using 7-hydroxyneryldiethylamine in place of the 7-hydroxygeranyldiethylamine used in Example 1, 65 g (yield: 86%) of 7-hydroxycitronellal was obtained.

EXAMPLES 15 TO 17

Table 4 shows results obtained in the same manner as in Example 1, except using the 7-hydroxygeranylamine listed in Table 4 in place of 7-hydroxygeranyldiethylamine used in Example 1.

TABLE 4

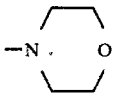

| Example | $R_1$ in Formula (I) $-N\langle{}^{R_1}_{R_2}$ | Yield (%) of 7-Hydroxycitronellal |
|---|---|---|
| 15 | 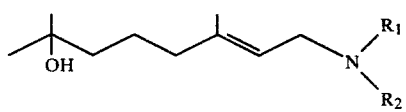 | 65 |
| 16 | 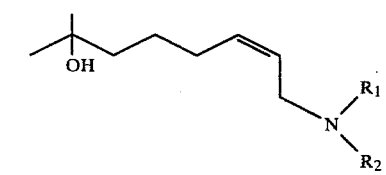 | 72 |
| 17 | —N(n-C$_4$H$_9$)$_2$ | 55 |

While the invention has been described in detail and with reference to specific embodiments thereof, it will be apparent to one skilled in the art that various changes and modifications can be made therein without departing from the spirit and scope thereof.

What is claimed is:

1. A process for preparing hydroxycitronellal comprising isomerizing a 7-hydroxygeranylamine compound (I) or a 7-hydroxynerylamine compound (II), represented by formulae (I) and (II), respectively,

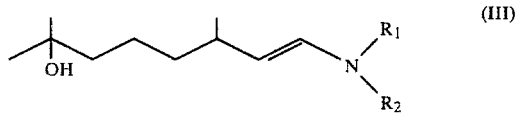

wherein $R_1$ and $R_2$ each represents an alkyl group containing from 1 to 6 carbon atoms or a cycloalkyl group, or $R_1$ and $R_2$ may jointly form together with the adjacent nitrogen atom a 5- or 6-membered ring that may contain other heterocyclic atoms selected from nitrogen and oxygen, using a catalytically effective amount of a catalyst composed of a divalent palladium compound and a phosphine compound at a temperature of from about 140° to 180° C. for about 5 to 20 hours, to thereby convert the amine compound to a 7-hydroxyaldehydoenamine represented by formula (III)

wherein $R_1$ and $R_2$ are the same as defined above, and then hydrolyzing the enamine using a dilute acid.

2. A process as in claim 1, wherein said catalyst composed of a divalent palladium compound and a phosphine compound is that obtained by reacting, in relative amounts, 1 mol of palladium compound, from 1 to 2 mols of a trivalent organophosphorous compound, and from 1 to 5 mols of an alkali metal phenoxide.

3. A process as in claim 2, wherein said trivalent organophosphorous compound is a compound represented by formula (IV)

$$P{-}B\genfrac{}{}{0pt}{}{\diagup A}{\diagdown C} \qquad (IV)$$

wherein A represents an alkyl group containing from 1 to 6 carbon atoms, a cycloalkyl group, or an aryl group, and B and C each represents an alkyl group containing from 1 to 6 carbon atoms, a cycloalkyl group, or an aryl group, or B and C may jointly form together with the adjacent phosphorus atom a 5- or 6-membered ring.

4. A process as in claim 2, wherein said trivalent organophosphorous compound is an alkylenediphosphine in which two phosphorus atoms are connected to each other through a carbon chain containing from 1 to 4 carbon atoms.

5. A process as in claim 2, wherein said trivalent organophosphorous compound is a diphosphine compound in which two phosphorus atoms form a heterocyclic ring.

6. A process as in claim 2, wherein said trivalent organophosphorous compound is 1,1'-bis-phosphinoferrocene in which two phosphorus atoms are connected to each other through a ferrocenyl group.

7. A process as in claim 2, wherein said alkali metal phenoxide is derived from unsubstituted, mono-substituted, di-substituted, or tri-substituted phenol.

8. A process as in claim 1, 2, 3, 4, 5, 6, or 7, wherein the molar ratio of the compound according to formula (I) or (II) to the palladium compound is from 1000/1 to 5,000/1.

9. A process as in claim 2, 3, 4, 5, 6, or 7, wherein the catalyst is obtained by reacting the organophosphorous compound and the palladium compound in a molar ratio of from 1/1 to 2/1, and, after dissolving in a solvent to prepare a homogeneous solution, adding thereto 1 to 5 moles of alkali metal phenoxide while cooling to a temperature of from 0° C. to 10° C.

10. A process as in claim 1, wherein said dilute acid is a mineral acid or an organic acid.

11. A process as in claim 10, wherein said mineral acid is hydrochloric acid, sulfuric acid or phosphoric acid and said organic acid is acetic acid.

* * * * *